United States Patent
Mulchandani

[19]

[11] Patent Number: 5,938,917
[45] Date of Patent: Aug. 17, 1999

[54] ELECTRODES FOR MEASUREMENT OF PEROXIDES

[75] Inventor: Ashok Kimatrai Mulchandani, Riverside, Calif.

[73] Assignee: The Regents of the University of California, Oakland, Calif.

[21] Appl. No.: 08/856,707

[22] Filed: May 15, 1997

Related U.S. Application Data

[63] Continuation of application No. 08/417,342, Apr. 5, 1995, abandoned.

[51] Int. Cl.$^6$ ..................................................... G01N 27/26
[52] U.S. Cl. ......................... 205/782; 204/403; 204/418; 205/775; 205/777.5; 205/787
[58] Field of Search ................................. 204/403, 416, 204/418, 419; 205/775, 792, 777.5, 782, 787

[56] References Cited

U.S. PATENT DOCUMENTS

| | | | |
|---|---|---|---|
| 4,871,442 | 10/1989 | Yamaguchi et al. | 204/418 |
| 5,061,976 | 10/1991 | Shimomura et al. | 204/418 |

OTHER PUBLICATIONS

Guilbault, G.G. & Lubarano, G.J., *Anal. Chim. Acta* 1973, 64, 439–455.
Cosgrove, M. et al., *Analyst* 1988, 113, 1811–1815.
Funk, M.O. et al., *Anal. Chem.* 1980, 52, 771–773.
White, S.F. et al., *Electroanalysis* 1994, 6, 625–632.
Hajizadeh, K. et al., *Anal. Chim. Acta* 1991, 243, 23–32.
Cox, J.A. & Jaworski, R.K., *Anal. Chem.* 1989, 61, 2176–2178.
Qi, X & Baldwin, R.P., *Electroanalysis* 1993, 5, 547–554.
Wang, J. et al., *Anal. Chim. Acta* 1991, 254, 81–88.
Gorton, L. et al., *Analyst* 1992, 117, 1235–1241.
Mulchandani, A. & Rudolph, D.C., *Anal. Biochem.* 1995, 225, 277–282.
Horwitz, C.P. & Dailey, G.C., *Chem. Mater.* 1990, 2, 343–346.
Gupta, B.L., *Microchem. J.* 1973, 18, 363–374.
Jiang, Z–Y. et al., *Anal. Biochem.* 1992, 202, 384–389.
Cosgrove, M. et al., *Analyst* 1989, 114, 1627–1632.
Rudzinski et al., *J. Electroanal. Chem.* 1992, 335, 265–279.
Gorton, L. et al., *J. Molecular Catalyst* 1986, 38, 49–60.
Mulchandani, A. & Wang, C.–L., *Anal. Chem.* 1995, 67, 94–100.
Horowitz et al., *J. Electroanal. Chem.* 1992, 324, 79–91.
Shimada et al., *J.of Chromatography* 1989, 487, 247–255.
Wang, C–L., et al., "Ferrocene–Conjugated Polyaniline–Modified Enzyme Electrodes for Determination of Peroxides in Organic Media", *Anal. Chem.*, 67:1109–1114 (1995) Month Unavailable.
Cass et al, "Eerrocene–Mediated Enzyme Electrode for Amperometric Determination of Glucose", *Anal. Chem.*, (1984) Month Unavailable, vol. 56, pp. 667–671.

*Primary Examiner*—T. Tung
*Attorney, Agent, or Firm*—Fulbright & Jaworski L.L.P.

[57] ABSTRACT

An electrode characterized by a layer of at least one polymer containing ferrocenylalkyl groups. The electrodes are useful in detecting hydrogen peroxide, organic (hydro)peroxides and lipid hydroperoxides.

13 Claims, 6 Drawing Sheets

ELECTRODES FOR MEASUREMENT OF PEROXIDES

This application is a continuation of application Ser. No. 08/417,342, filed Apr. 5, 1995, now abandoned.

BACKGROUND OF THE INVENTION

The present invention relates generally to the fields of chemistry, chemical engineering, process and environmental monitoring, food industry and medicine. More particularly, the present invention is directed to electrodes for determination of the presence of peroxides, as well as methods for the preparation and use thereof.

There is a growing need for sensitive, selective and accurate measurement of hydrogen peroxide, organic (hydro)peroxides and lipid hydroperoxides in clinical, pharmaceutical, food and industrial processes and environmental applications. For example, the development of flavin enzyme-based assays or electrodes require sensitive measurement of $H_2O_2$ formed in enzyme catalyzed reactions [Guilbault, G. G. & Lubarano, G. J., Anal. Chim. Acta 1973, 64, 439–455]. $H_2O_2$ determination is also important to ensure the safety and quality of pharmaceutical and cosmetic formulations [Wang, J. et al., Analyst 1993, 118, 277–280]. Measurement of lipid hydroperoxides, the primary products of lipid peroxidation, is of great medical significance in connection with cancer development, aging processes and other pathological conditions [Mannino, S. et al., Anal. Lett. 1994, 27, 299–308; Eun, J. -B. et al., J. Food Sci. 1994, 59, 251–255; Shantha, N. C. & Decker, E. A., J. AOAC International 1994, 77, 421–424; Roozen, J. P. & Linssen, J. P. H., In Lipid Oxidation in Food. ACS Symposium Series 500, St. Angelo, A. J., Ed., American Chemical Society: Washington, D.C., 1992, Chapter 17 & 18, pp. 302–321; Hageman, G. et al., Lipids 1989, 24, 899–902]. Monitoring of organic (hydro)peroxides formed during the reaction of ozone with organic compounds in the atmosphere and drinking water or directly released into the environment from numerous industrial processes is desirable because of their adverse health effects [*IARC Monographs on the Evaluation of the Carcinogenic Risk of Chemicals to Humans. Allyl Compounds, Aldehydes, Epoxides and Peroxides*, IARC: Lyon, France, 1985, Vol. 36, pp. 267–321; Glaze, W. H., Environ. Sci. Technol. 1987, 21, 224–230; Kok, G. L. et al., Environ. Sci. Technol. 1978, 12, 1072–1076].

Conventionally titrimetric [Bassett, J. et al., In *Textbook of Quantitative Inorganic Analysis*, Vogel, A. I., Ed., 4th edition, Longman: London, 1978, p. 355], spectrophotometric [Sellers, R. M., Analyst 1980, 105, 950–954], colorimetric [Ito, Y. et al., Assoc. Off. Anal. Chem. 1981, 64, 1448–1452], chemiluminescent [Kok, G. L. et al., Environ. Sci. Technol. 1978, 12, 1072–1076] and amperometric methods are used for the detection and measurement of peroxides. Because of the very low detection limits, amperometry is the most widely used technique [Yamada, K. et al., Lipids 1987, 22, 125–128]. Amperometric determinations of peroxides are generally performed by oxidation at +0.6 to +0.7 V vs. Ag/AgCl on a platinum electrode (for $H_2O_2$) [Guilbault & Lubarano (1973), supra] or reduction at –0.3 to –1.0 V vs. Ag/AgCl on gold/mercury amalgam or glassy carbon electrode (for organic and lipid hydroperoxides) [Cosgrove, M. et al., Analyst 1988, 113, 1811–1815; Funk, M. O. et al., Anal. Chem. 1980, 52, 773–774]. At such large overpotentials, substances such as ascorbic acid, uric acid and acetaminophen interfere under oxidation conditions, while oxygen and compounds such as benzoquinone, nitrobenzene, etc., interfere at reduction potentials. Low selectivity is therefore a major limitation in amperometric determinations.

To overcome the limitations imposed by the requirement of large overpotentials on the selectivity of these sensors, different approaches have been proposed. Platinized and rhodinised carbon electrodes have been developed to lower the oxidation potential for $H_2O_2$ to +0.4 V [White, S. F. et al., Electroanalysis 1994, 6, 625–632]. Although the oxidation potential for $H_2O_2$ on such electrodes is lowered, detection is still not completely free of interference [Hajizadeh, K. et al., Anal. Chim. Acta 1991, 243, 23–32]. Determination of $H_2O_2$ by reduction at electrodes modified with $Ru(NH_3)_6^{3+}$-incorporated montmorillonite clay [Oyama, N. & Anson, F. C., J.Electroanal.Chem. 1986, 199, 467–470], palladium/iridium [Cox, J. A. & Jaworski, R. K., Anal. Chem. 1989, 61, 2176–2178] and iron phthalocyanine [Qi, X. & Baldwin, R. P., Electroanalysis 1993, 5, 547–554] have been reported. These electrodes, however, have limitations. The determination of $H_2O_2$ at the Pd/Ir modified electrode is performed at –0.3 V (vs. Ag/AgCl) at which dissolved oxygen is also reduced and therefore interferes. Reductions of $H_2O_2$ at $Ru(NH_3)_6^{3+}$-incorporated montmorillonite clay and iron phthalocyanine modified electrodes require strongly acidic environment (pH 2) and therefore limit the application of these electrodes for construction of flavin enzyme-based biosensors. Iron phthalocyanine modified electrodes have also been used to detect organic (hydro) peroxides at lower reduction potential [Qi, X. & Baldwin, R. P., supra].

Use of enzyme (peroxidase) modified electrodes to determine $H_2O_2$, organic (hydro)peroxides and lipid hydroperoxides by reduction have been reported. These enzyme modified electrodes, operating between 0 and –0.2 V vs. Ag/AgCl, are reported to be free of interference from ascorbate, urate and paracetamol [Mannino et al. (1994), supra; Cosgrove et al. (1988), supra Kulys, J. J. et al., Bioelectrochem. Bioenerg. 1981, 8, 81–88; Wang, J. et al., Anal. Chim. Acta 1991, 254, 81–88; Vreeke, M. et al., Anal. Chem. 1992, 64, 3084–3090; Wollenberger, U. et al., Anal. Lett. 1990, 23, 1795–1808; Gorton, L. et al., Analyst 1992, 117, 1235–1241; Mori, H. et al., Anal. Lett. 1992, 25, 1643–1656. Nonetheless, the use of the heretofore known enzyme peroxidase electrodes also entails disadvantages, such as short shelf-life.

It is an object of the present invention to provide electrodes which do not suffer from all of the drawbacks of the prior art electrodes, as well as methods for the preparation and use thereof.

SUMMARY OF THE INVENTION

In accordance with the present invention, electrodes useful for determination of hydrogen and organic (hydro) peroxides and lipid hydroperoxides by reduction at low applied potential are provided. The electrodes are characterized by a layer of at least one polymer comprising a ferrocenylalkyl (preferably, ferrocenyl-lower-alkyl) group. Suitably, such a polymer may be based on at least one monomer having the general formula I $$A\text{-}(CRR')_n\text{-}B$$

wherein A is a polymerizable group (i.e., one having a structure amendable to polymerization); B is a ferrocenyl group; each of R and R' is independently selected from the group consisting of H and lower alkyl; and n is an integer less than about 20, preferably 1–5. A variety of conventional electrode substrates may be employed, including but not limited to metal (platinum, gold, etc.), carbon (glassy and graphite) and screen printed electrode substrates. In a preferred embodiment, the electrodes are poly (anilinomethylferrocene) modified glassy carbon electrodes.

BRIEF DESCRIPTION OF THE DRAWINGS

The invention may be better understood with reference to the accompanying drawings, in which.

DETAILED DESCRIPTION OF THE INVENTION

Figure 1:
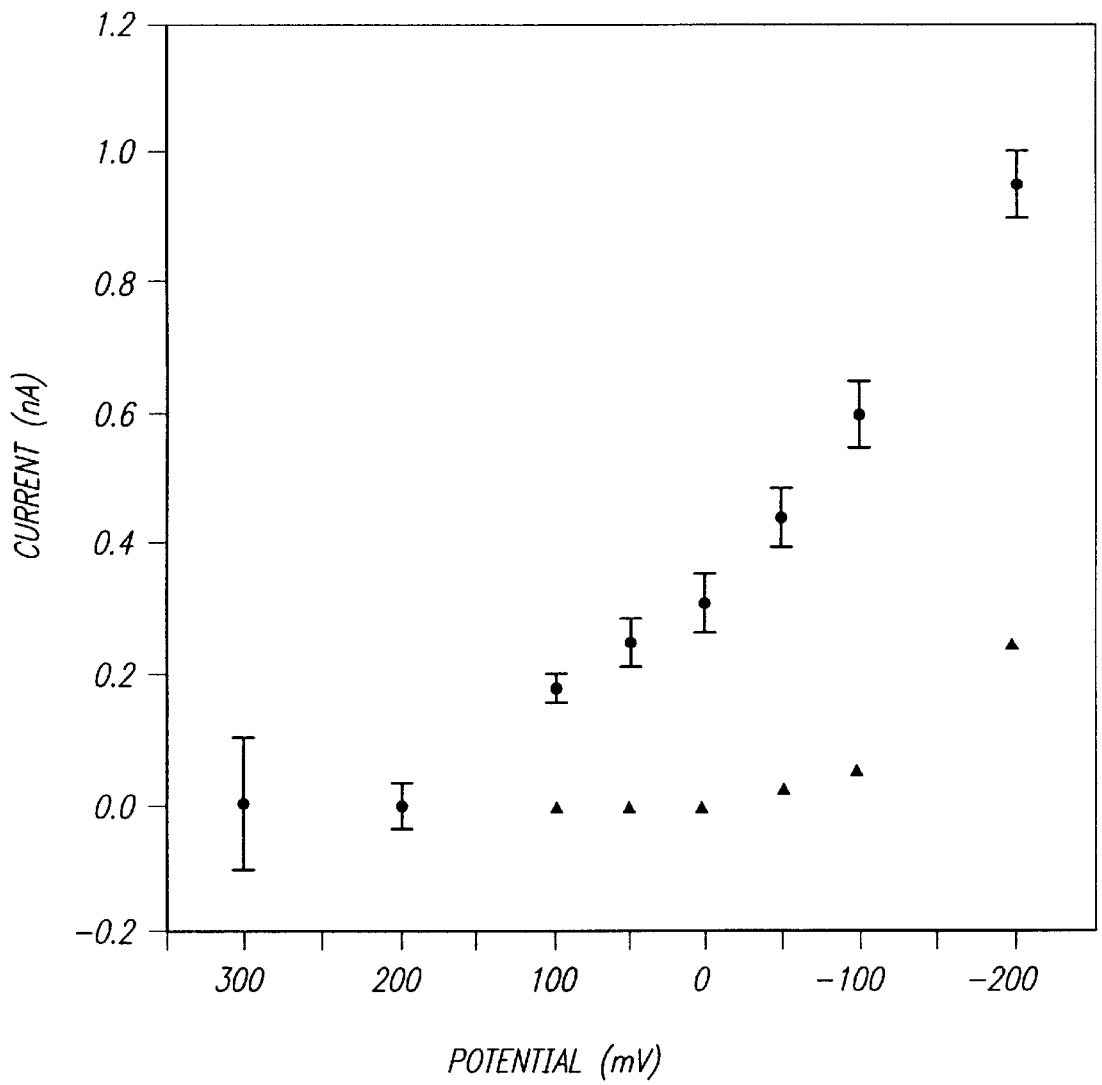
FIG. 1 illustrates the effect of operating potential on the response of the poly(AMFc) modified electrode to (●) 10 $\mu$M $H_2O_2$ and (▲) 10 $\mu$L injections of water in deaerated (10 mL) 0.05 M MES pH 5.5 buffer with 0.1 M $NaClO_4$ (data points are average of three measurements and the error bars represent ±1 standard deviation)

Pursuant to the present invention, electrodes for cathodic determination of hydrogen peroxide, organic peroxides and fatty acid hydroperoxides are provided. These electrodes are characterized by a layer of at least one polymer comprising a ferrocenylalkyl (preferably, ferrocenyl-lower-alkyl) group. Suitably, such a polymer may be based on at least one monomer having the general formula I A-(CRR')$_n$-B wherein A is a polymerizable group (i.e., one having a structure amendable to polymerization); B is a ferrocenyl group; each of R and R' is independently selected from the group consisting of H and lower alkyl; and n is an integer less than about 20, preferably 1–5. In one preferred embodiment, A is anilino ($C_6H_5NH$-), both R and R' are H and n is 1.

The monomers of general formula I may be synthesized by a variety of alternative heretofore known techniques, as would be readily appreciated by one skilled in the art. Suitable polymers for use in accordance with the present invention typically comprise at least about 0.001 mol-%, more preferably at least about 0.01 mol-%, and most preferably about 0.1 mol-% to about 100 mol-% of a monomer of general formula I.

Exemplary electrodes were constructed by modifying the surface of a glassy carbon electrode with an electrochemically deposited ferrocene-modified polyaniline film from a solution of N(ferrocenylmethyl)aniline monomer in acetonitrile:

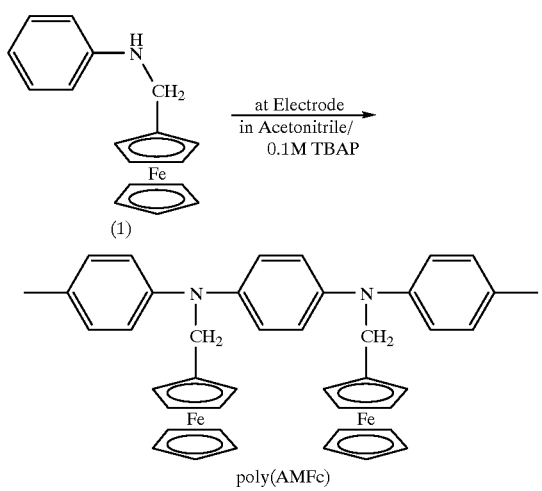

Of course, alternative methods as are well known to those working in the field may also be employed to prepare electrodes in accordance with the present invention. For example, the monomer(s) may be polymerized chemically and then an electrode substrate surfaced modified by spin coating.

Hydrodynamic voltametry studies showed that both hydrogen peroxide and oxygen were reduced at the electrode with an increasing response at higher cathodic potentials. The interference due to molecular oxygen was minimized at −50 mV vs. Ag/AgCl. At this potential the electrode also responded to organic (hydro)peroxides (e.g., cumene hydroperoxide, tert-butyl hydroperoxide and 2-butanone peroxide), to linolenic acid hydroperoxide in both aqueous and organic medium and to lauroyl peroxide in organic medium. The response of the exemplary electrodes was a function of the thickness of the poly (anilinomethylferrocene) film, pH of the electrolyte, and (for organic phase analytes) the amount of aqueous medium.

In general, the layer of polymer in the electrodes of the present invention has a thickness of about 10 nm to about 500 nm, preferably about 30 nm to about 100 nm. A suitable layer having the requisite thickness for a given composition may be identified by, e.g., electrochemical quartz crystal balance and scanning electron microscope. The electrode substrate may be of any conventional design and composition suitable for construction of an operative electrode; in one preferred embodiment, the electrode substrate is a conventional glassy carbon electrode (as is commercially available from, for example, Bioanalytical Systems Inc., Lafayette, Ind. under the designations MF 2012 and MF 1000). The electrodes of the present invention are generally free from interference due to electroactive compounds such as ascorbic and uric acids.

The electrodes of the present invention may advantageously be used to determine hydrogen peroxide and organic peroxides at low applied potential in both aqueous media over a wide pH range (e.g., pH 2–7) and organic media. The electrodes provide a means for determining these analytes with high sensitivity and without interference from electroactive compounds such as ascorbic acid, uric acid and oxygen.

Chemical modification of the electrode surface through electrochemical polymerization further enables construction of ultramicroelectrodes and electrodes of complex three dimensional geometry, such as reticulated surfaces, in a conventional manner.

The electrodes of the present invention have particular application in the construction of sensitive and selective sensors [eg., enzyme electrodes for the determination of hydrogen peroxide produced in flavin enzyme (such as glucose oxidase) catalyzed reactions]. The electrodes are also useful in chemical sensors for environmental monitoring, chemical process monitoring, clinical diagnosis and food quality assessment.

The invention may be better understood with reference to the accompanying example, which is intended for purposes of illustration only and should not be construed as in any sense limiting the scope of the present invention as defined in the claims appended hereto.

EXAMPLE (2-[N-Morpholino]ethanesulfonic acid) monohydrate (MES), glucose oxidase (EC 1.1.3.4) type VII from *Aspergillus niger* (activity 1682 U/g solid), lipoxidase (EC 1.13.11.12) type I-B from soybean (150,000 U/mg protein) and linolenic acid were purchased from Sigma Chemical Co. (St. Louis, Mo.). Sodium phosphate monobasic monohydrate, sodium phosphate dibasic anhydrous, citric acid monohydrate, acetonitrile (HPLC grade), tetrabutylammonium perchlorate (TBAP), glutaraldehyde (25% in water) and hydrogen peroxide (30% in water) were obtained from Fisher Scientific (Tustin, Calif.). Aniline, 1,2 phenylenediamine, resorcinol, cumene hydroperoxide, tert-butyl hydroperoxide, 2-butanone peroxide and lauroyl peroxide were acquired from Aldrich (Milwaukee, Wis.). All the chemicals were used without purification. Double distilled ultrapure water was used for preparation of the buffers, standards and electrochemistry work.

For synthesis of N-(ferrocenylmethyl)aniline monomer I, 15 mL of aniline was mixed with 5 g of [(N,N-dimethylamino)-methyl] ferrocene methiodide in water and refluxed for 3 h. when a reddish orange viscous oil was formed. After cooling, the water was decanted and the oily layer extracted in ethyl ether. This layer was then dried overnight on sodium sulfate and chromatographed on silica gel using a 1:1 mixture of ethyl acetate and hexane. The first band containing the desired product was collected, and after evaporating the solvent, the residue was dissolved in petroleum ether and the product crystallized by cooling in the refrigerator to 4° C.

Linolenic acid hydroperoxide was prepared by oxidizing the fatty acid in presence of lipoxidase according to the reported procedure [Mulchandani, A. & Rudolph, D. C., *Anal. Biochem.* 1995, 225, 277–282].

Glassy carbon electrodes ("GCES") (Bioanalytical Systems Inc., Lafayette, Ind.) were polished with 1 μm diamond paste followed by 0.05 μm γ-alumina particles (Buehler, Lake Bluff, Ill.). Electrodes were rinsed with water and ultrasonicated for 2–5 min after each polishing step.

A poly(anilinomethylferrocene) ["poly(AMFc)"] film was deposited on the prepared GCE from an electrolyte bath containing 5 mM I and 0.1 M TBAP in acetonitrile, which was deaerated with argon prior to electropolymerization, by cycling the electrode potential at 100 mV s$^{-1}$ between 0 and 1.1 V vs. Ag/AgCl for the desired number of cycles. The electrode was then rinsed with acetonitrile to remove entrapped monomer and TBAP and stored dry.

Polyaniline modified GCEs were prepared by depositing polyaniline film on polished GCE from 0.1 M aniline in 1.0 M perchloric acid and 0.1 M aniline plus 0.2 M TBAP in acetonitrile by cycling the potential at 100 mV s$^{-1}$ between –0.2 and 0.9 V vs. Ag/AgCl for 5 cycles.

Glucose enzyme electrodes were constructed by immobilizing glucose oxidase on the top of the poly(AMFc) film by crosslinking with glutaraldehyde and subsequent entrapment in a 1,2-phenylenediamine-resorcinol polymer film. 3 μl of a mixture containing 45 μg of glucose oxidase enzyme and 1% (w/v) glutaraldehyde in 0.1 M pH 6.5 phosphate buffer was added on the top of the poly(AMFc) film and allowed to dry for 2 h at room temperature. Subsequently, this electrode was made the working electrode in an electrochemical cell containing deaerated solution of 1.5 mM each of resorcinol and 1,2-phenylenediamine monomers in 0.1 M pH 6.5 phosphate buffer with 0.1 M NaClO$_4$. The potential was cycled between 0 and +0.65 V vs. Ag/AgCl at a scan rate of 20 mV/s for 8 cycles to deposit a polymer film. The electrode was washed in 0.1 M pH 5.5 citrate-phosphate to remove any free enzyme and monomers.

Electropolymerizations were performed under stationary conditions in a 10 ml electrochemical cell placed inside a Faraday cage (BAS, C-2) with a potentiostat/galvanostat (263A, EG&G, Princeton, N.J.) interfaced to an 80486-based personal computer. Batch amperometric measurements were performed in a 10 ml electrochemical cell placed inside a Faraday cage (BAS, C-2) under stirred conditions with a Voltammogaph (BAS, CV 27) coupled to a low current module (BAS, PA1-Preamplifier). The signals were recorded on a X-Y-t chart recorder (BAS, MF-8051). All measurements were performed with Ag/AgCl reference and platinum auxiliary electrodes in either 0.1 M citrate-phosphate buffer with 0.1 M NaClO$_4$, 0.05 mM pH 5.5 MES buffer with 0.1 M NaClO$_4$, pure acetonitrile with 0.1 M TBAP or 90% acetonitrile plus 10% 0.05 M pH 5.5 MES buffer with 0.1 M TBAP.

Flow-injection analysis (FIA) was performed using a thin-layer flow cell (BAS, CC-5) with dual glassy carbon working electrode, Ag/AgCl reference electrode and stainless steel counter electrode. The electrode was poised at –50 mV using a potentiostat (BAS, LC-4C) and the output recorded on a flat-bed chart recorder (BD-112, Kipp and Zonen, Delft, Holland). A multi-channel precision flow peristaltic pump (EVA Pump, Eppendorf North America, Madison, Wis.) was used to deliver the appropriate mobile phase and sample. A 20 μL sample was injected into the mobile phase by a motorized injection valve (EVA-Inject Valve, Eppendorf North America, Madison, Wis.).

FIG. 1 shows the dependence of the poly(AMFc) modified electrode response on the applied potential to additions of deaerated H$_2$O$_2$ solution and non-deaerated water to deaerated 0.05 M pH 5.5 MES buffer with 0.1 M NaClO$_4$ in the electrochemical cell. In presence of H$_2$O$_2$, while there was no response between +0.3 and +0.2 V, the response increased rapidly as the potential was made more cathodic to –0.2 V. When evaluated for response to non-deaerated water over the same potential range, the poly(AMFc) electrode had no response between potentials of +0.3 and –0.05 V and a small cathodic response at potentials of –0.1 and –0.2 V. The response at −0.1 and −0.2 V is attributed to the reduction of molecular oxygen at the poly(AMFc) modified electrode. The potential of −0.05 V, at which there was no significant interference due to oxygen reduction, was therefore selected as the operating potential in subsequent work.

Figure 2:
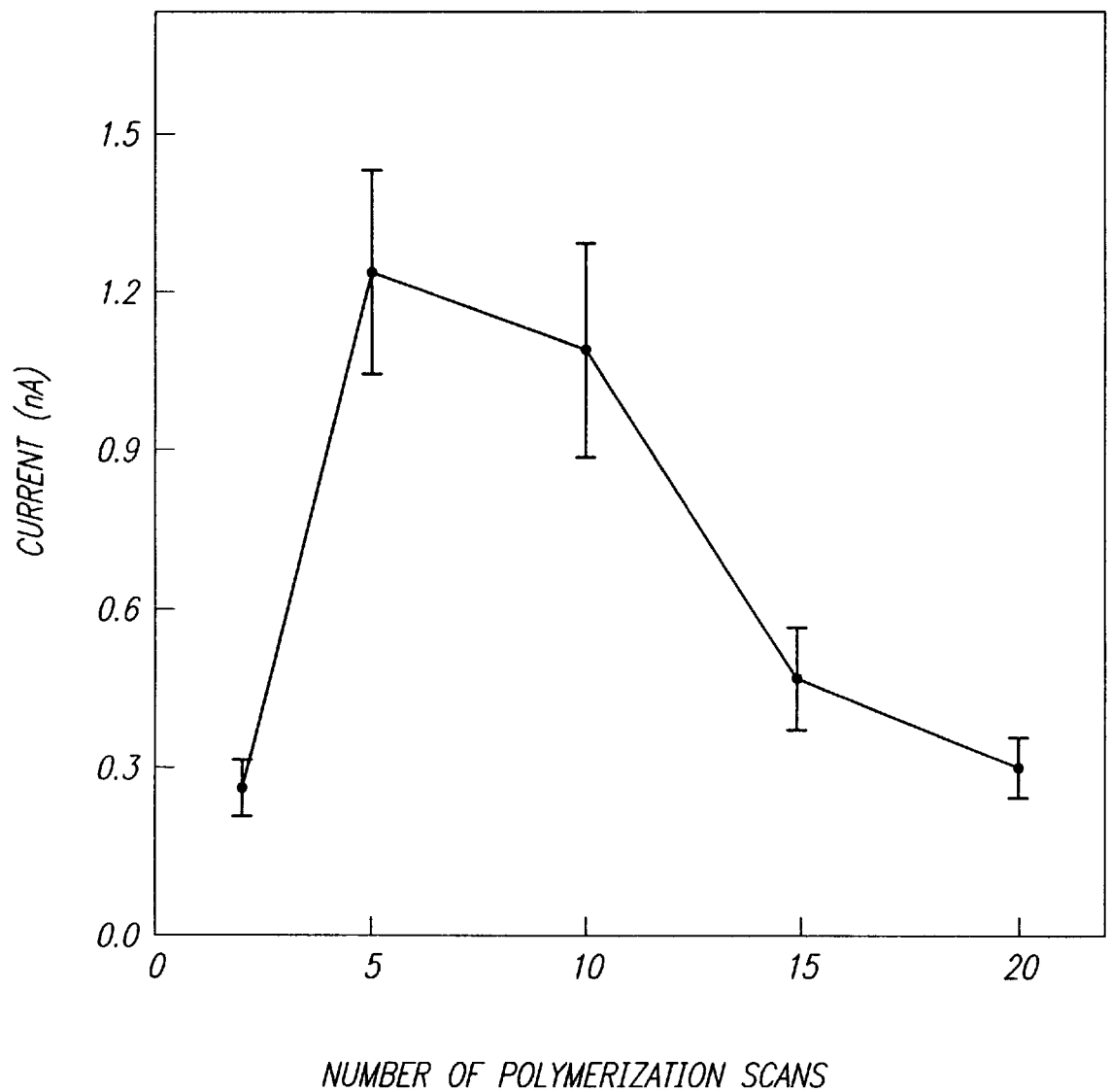
FIG. 2 illustrates the effect of number of polymerization scans on the cathodic response of the poly(AMFc) modified electrode to 10 $\mu$M $H_2O_2$ in pH 5.5 0.1 M MES buffer with 0.1 M $NaClO_4$ at −50 mV vs Ag/AgCl reference (data points are average of 3 measurements and the error bars represent ±1 standard deviation)

FIG. 2 shows the plot of the cathodic response of the poly(AMFc) modified electrode to $H_2O_2$ as a function of the number of polymerization scans used for depositing the polymer film. As expected, due to the higher ferrocene surface coverage, the response initially increased with an increase in number of polymerization scans. However, on further increase in number of polymerization scans, the response decreased. This decrease is presumably associated with charge transfer limitations arising due to a thicker polymer film deposited on the GCE with increasing numbers of polymerization scans. No attempts were made to determine the thickness of deposited films. Electrodes constructed using 5 polymerization scans were used in subsequent studies.

Figure 3:
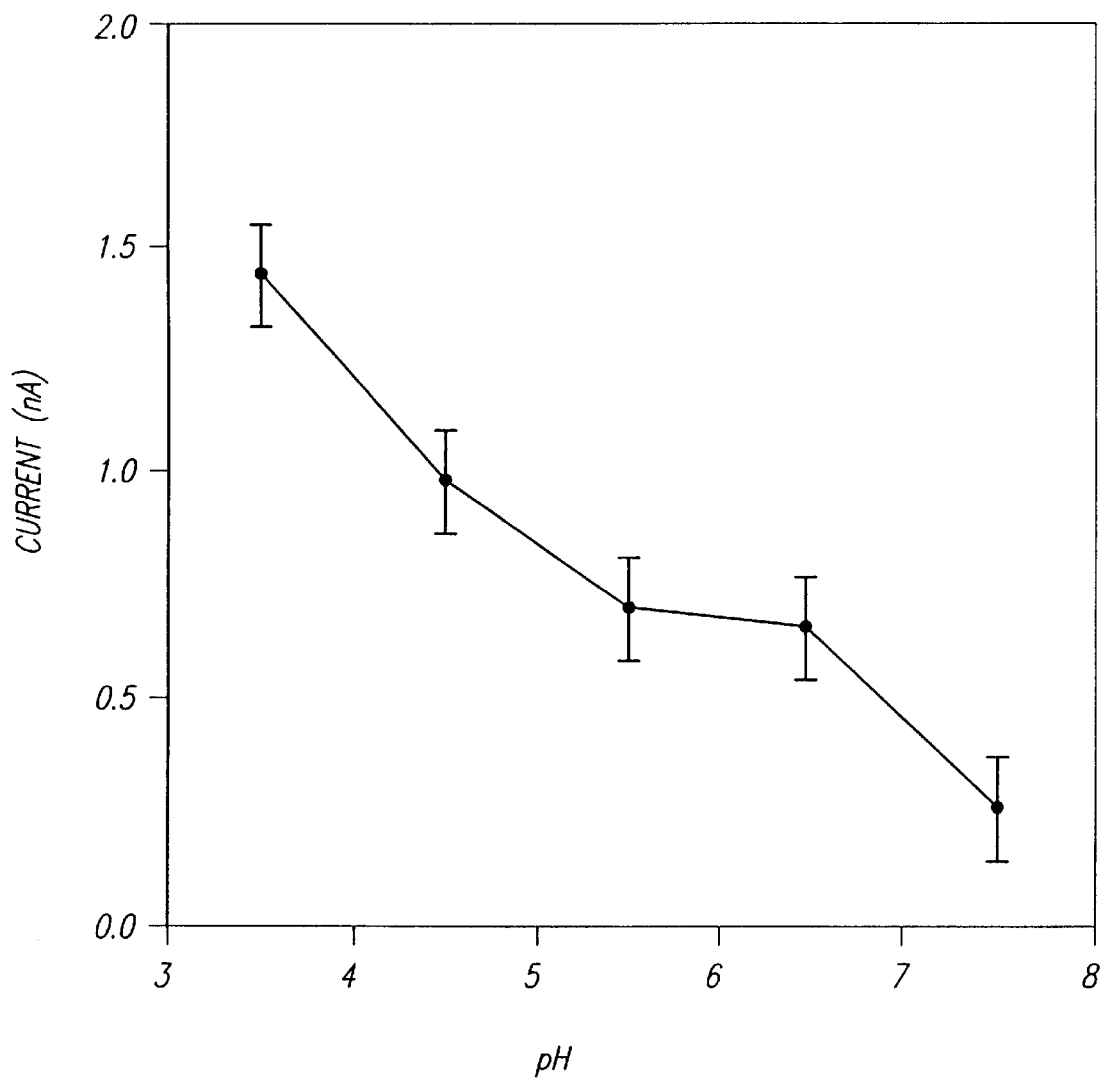
FIG. 3 illustrates the effect of the solution pH on the cathodic response of the poly(AMFc) modified electrode to 10 $\mu$M $H_2O_2$ at −50 mV vs Ag/AgCl reference, electrolyte: 0.15 M $NaClO_4$ solution adjusted to the desired pH by HCl or NaOH (data points are average of 3 measurements and the error bars represent ±1 standard deviation)

The cathodic response of the poly(AMFc) modified electrode to $H_2O_2$ increased as the pH of the measuring electrolyte was lowered (FIG. 3). This inverse relationship between the cathodic response and the electrolyte pH can be attributed to the increase in the conductivity of the polyaniline backbone of poly(AMFc) [Horwitz, C. P. & Dailey, G. C., Chem. Mater. 1990, 2, 343–346; Deshpande, M. V. & Amalnerkar, D. P., Prog. Polym. Sci. 1993, 18, 623–649]. The ability of the poly(AMFc)-modified electrode to monitor $H_2O_2$ over a wide pH range demonstrates its applicability in construction of oxidase enzyme-based amperometric biosensors.

Control experiments were performed to investigate if GCEs modified with polyaniline alone responded to $H_2O_2$ at the selected potential (−50 mV) and pH (5.5). Electrodes modified with polyaniline films grown from aniline solution in acetonitrile and pH 1.0 aqueous medium did not respond. These results are in agreement with a previous report [Doubova, L. et al., Electrochim. Acta 1989, 34, 337–343] that even at low pH the cathodic reduction of $H_2O_2$ at the polyaniline modified electrode is extremely inhibited because of the very low kinetic efficiency of $H_2O_2$ for oxidizing aniline.

That the polyaniline modified electrode does not detect $H_2O_2$ by reduction, whereas the poly(AMFc) modified electrode does, led to a hypothesis that the ferrocene incorporated in the polyaniline film is oxidized by the peroxide to ferricinium which is then electroreduced at the electrode surface. This hypothesis is also based on literature reports that $H_2O_2$, organic peroxides and lipid peroxides can be determined by the oxidation of (a) Fe(II) to Fe(III) by peroxides at low pH (2.0), followed by complexation with xylenol orange and determination of the complex spectrophotometrically [Gupta, B. L., Microchem. J. 1973, 18, 363–374; Jiang, Z-Y. et al., Anal. Biochem. 1992, 202, 384–389] and (b) Fe(II)PC (iron phthalocyanine) incorporated in carbon paste to Fe(III)PC at pH 2.0, followed by electroreduction at +0.1 to 0.2 V vs Ag/AgCl [Qi & Baldwin (1993), supra].

Figure 4:
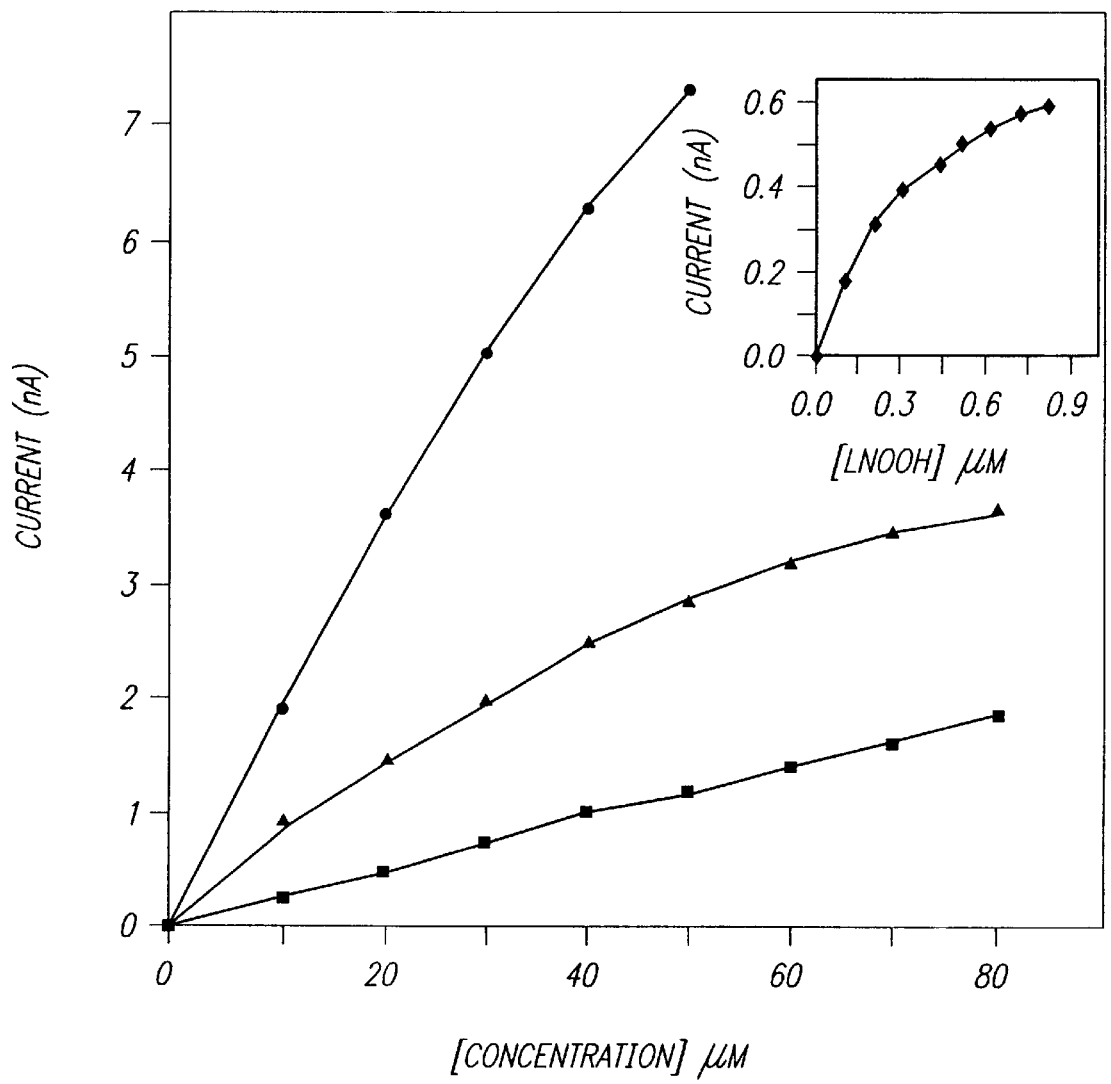
FIG. 4 illustrates calibration plots for (●) $H_2O_2$, (■) tert-butyl hydroperoxide, (▲) cumene hydroperoxide and (♦) linolenic acid hydroperoxide in pH 5.5 0.05 M MES buffer with 0.1 M $NaClO_4$, operating potential −50 mV vs Ag/AgCl (the points are average of measurements using two electrodes)

FIG. 4 and Table I show calibration plots and analytical features, respectively, of the poly(AMFc) electrode operating at −50 mV vs. Ag/AgCl in aqueous medium (0.05 M pH 5.5 NIES buffer with 0.1 M $NaClO_4$). The results show the versatility of the newly developed electrode in determining not only $H_2O_2$, but also organic (hydro)peroxides such as cumene hydroperoxide and tert-butyl hydroperoxide and an unsaturated fatty acid hydroperoxide, linolenic acid hydroperoxide. The precision of the electrode expressed in terms of the relative standard deviation was 3% for a concentration level of 25 μM $H_2O_2$ (n=25).

When used repeatedly for 100 analyses (25 μM $H_2O_2$) over a period of 2.5 h in a flow injection analyzer, the output response of the electrode gradually dropped to approximately 67% of the original response.

Figure 6:
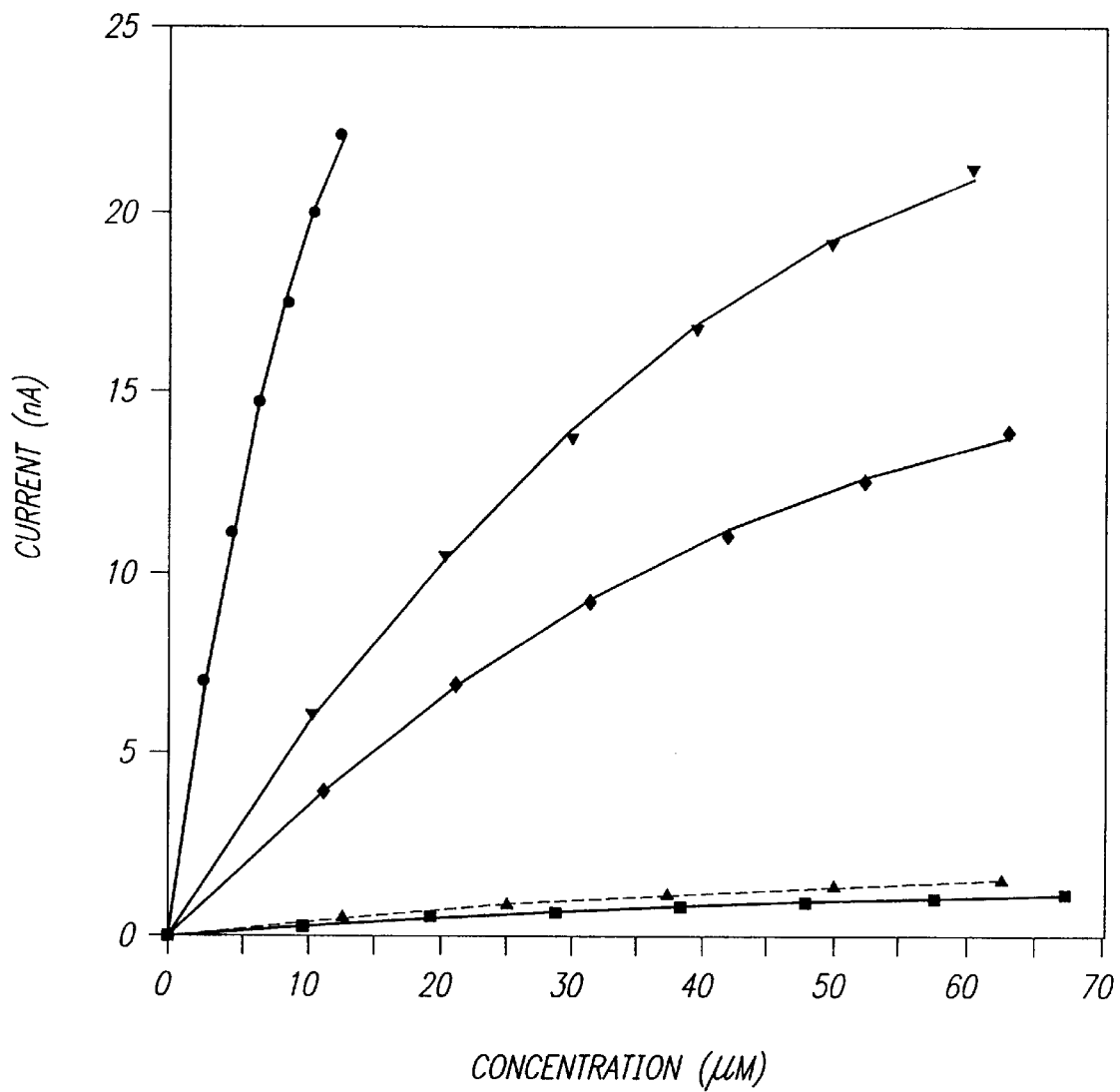
FIG. 6 illustrates calibration plots for (▼) $H_2O_2$, (●) lauroyl peroxide, (♦) 2-butanone peroxide, (▲) cumene hydroperoxide and (■) tert-butyl hydroperoxide in 90% acetonitrile with 0.1 M TBAP plus 10% 0.05 M pH 5.5 MES buffer with 0.1 M $NaClO_4$, operating potential −50 mV vs Ag/AgCl (the points are average of measurements using two electrodes).

In many applications the peroxide to be monitored is present in an organic matrix that is either not soluble or has very low solubility in aqueous media and therefore monitoring in organic media is preferable [Wang, C. -L. & Mulchandani, A., Anal. Chem. 1995, 67, 1109–1114]. Experiments were performed in organic media in order to evaluate the applicability of the poly(AMFc) electrode for such applications. The electrode was able to detect hydrophobic peroxides, lauroyl and 2-butanone peroxides, and $H_2O_2$ in pure acetonitrile and in a 90% acetonitrile and 10% 50 mM pH 5.5 MES buffer with 0.1 M TBAP mixture (Table 2). Since the response of the electrode to peroxides was higher in the 10% aqueous solution, experiments for electrode calibration plots (FIG. 6) were conducted in the above solution.

When the poly(AMFc) modified electrode was operated at pH 5.5 and at applied potential of −50 mV vs Ag/AgCl, the response to $H_2O_2$ was unaffected by the presence of 0.06 mM ascorbic acid and 0.03 mM uric acid.

Figure 5:
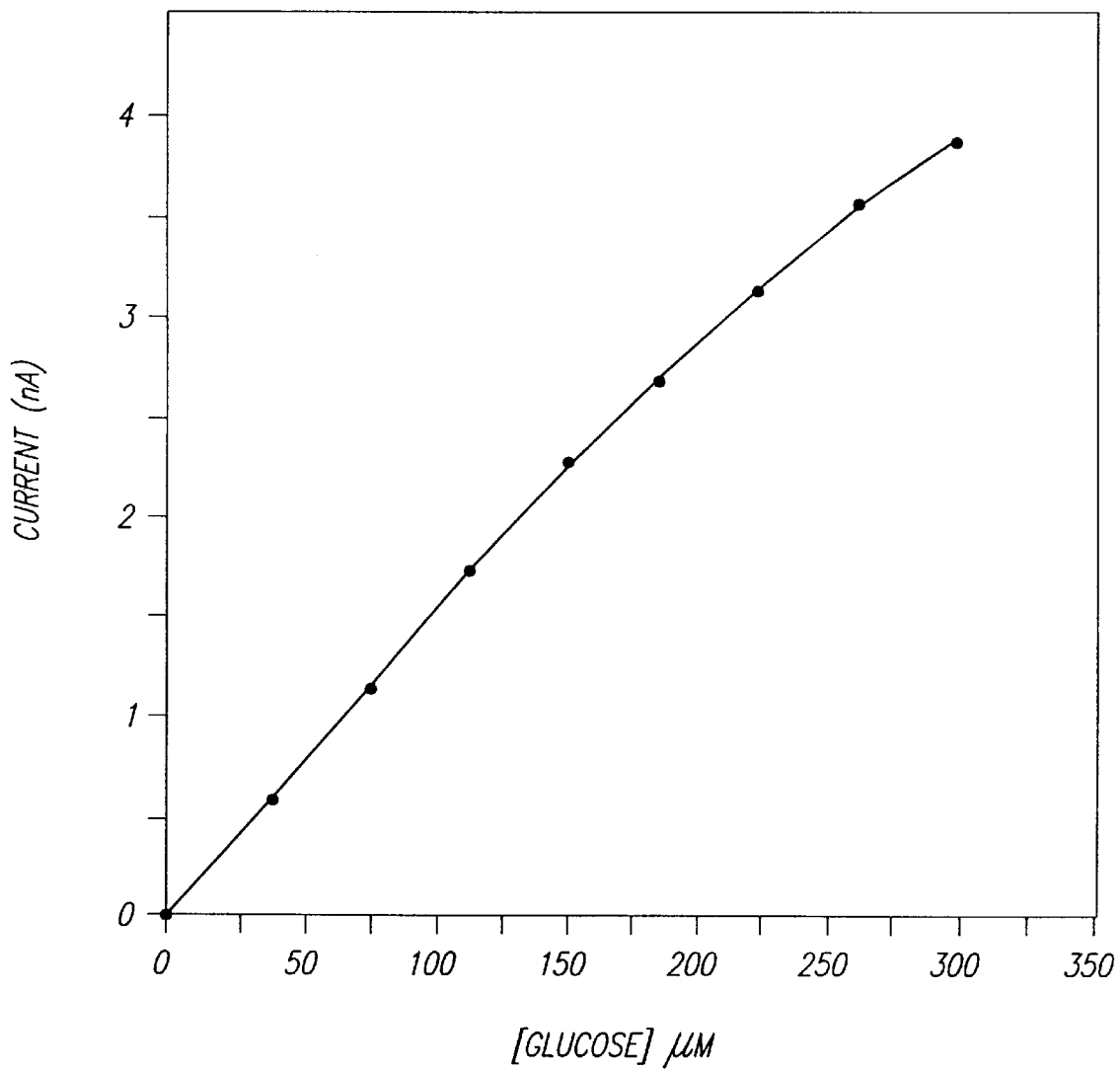
FIG. 5 illustrates calibration plots for (●) glucose in pH 5.5 0.05 M MES buffer with 0.1 M $NaClO_4$, operating potential −50 mV vs Ag/AgCl (the points are average of measurements using two electrodes)

The poly(AMFc) modified electrode was used in the construction of a flavin enzyme based biosensor. The calibration plot and characteristics of a glucose oxidase modified poly(AMFc) electrode for the determination of β D-glucose are shown in FIG. 5 and Table 1, respectively. Investigations into the response of the enzyme electrode to glucose in oxygen free medium showed that the electrode produced no response, confirming that the electrode response was only due to the $H_2O_2$ produced by the enzyme catalyzed reaction of glucose and oxygen. Similar to the $H_2O_2$ measurement, glucose measurements were not affected by the presence of 0.06 mM ascorbic acid and 0.03 mM uric acid.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

TABLE 1

Characteristics of calibration graphs for the poly (AMFc) modified electrode

| Analyte | Linear range (μM) | Sensitivity (nA μM$^{-1}$) | Intercept (nA) | $r^2$ |
|---|---|---|---|---|
| Hydrogen peroxide[a] | 0–30 | 0.167 | 0.127 | 0.9951 |
| tert-butyl hydroperoxide[a] | 0–80 | 0.023 | 0.029 | 0.9959 |
| Cumene hydroperoxide[a] | 0–20 | 0.066 | 0.119 | 0.9823 |
| Linolenic acid hydroperoxide[a] | 0–0.2 | 1.51 | 0.0075 | 0.993 |
| Glucose[a] | 0–190 | 0.0145 | 0.04 | 0.9959 |
| Hydrogen peroxide[b] | 0–20 | 0.535 | 0.285 | 0.9916 |

TABLE 1-continued

Characteristics of calibration graphs for the poly (AMFc) modified electrode

| Analyte | Linear range (μM) | Sensitivity (nA μM$^{-1}$) | Intercept (nA) | r$^2$ |
|---|---|---|---|---|
| Lauroyl peroxide[b] | 0–6 | 2.411 | 0.943 | 0.9744 |
| 2-butanone peroxide[b] | 0–20 | 0.327 | 0.207 | 0.9892 |
| tert-butyl hydroperoxide[b] | 0–60 | 0.018 | 0.043 | 0.9922 |
| Cumene hydroperoxide[b] | 0–50 | 0.026 | 0.052 | 0.9895 |

[a]in aqueous phase, 0.05 M MES pH 5.5 buffer with 0.1 M NaClO$_4$
[b]in 90% CH$_3$CN with 0.1 M TBAP and 10% 0.05 M MES pH 5.5 with 0.1 M NaClO$_4$

TABLE 2

Response of the poly (AMFc) modified electrode to peroxides in organic solvent

| Analyte | Concentration (μM) | 100% CH$_3$CN (nA) | 90% CH$_3$CN with 0.1 M TBAP and 10% 0.05 M MES with 0.1 M NaClO$_4$ (nA) |
|---|---|---|---|
| Hydrogen peroxide | 10 | 0.7 ± 0.09 | 2.79 ± 0.3 |
| Lauroyl peroxide | 2 | 1.08 ± 0.29 | 2.96 ± 0.47 |
| 2-butanone peroxide | 10 | 0.67 ± 0.12 | 2.34 ± 0.5 | n = 3

What is claimed is:

1. A method for selectively detecting a peroxide analyte, comprising:
   a) bringing a sample containing the peroxide analyte into contact with an electrode, the electrode comprising a substrate and a surface, the surface comprising a layer of at least one polymer containing ferrocenylalkyl groups;
   b) applying an electric potential to the sample;
   c) reducing the peroxide analyte in the sample at the electrode surface;
   and
   d) determining a response of the electrode to selectively detect the peroxide analyte present in the sample.

2. A method according to claim 1, wherein the peroxide analyte is selected from the group consisting of hydrogen peroxide, organic(hydro)peroxides, and lipid hydroperoxides.

3. A method according to claim 1, wherein the electrode surface further comprises an immobilized enzyme, which produces a peroxide reaction product.

4. A method according to claim 3 wherein the immobilized enzyme is glucose oxidase.

5. A method according to claim 1, wherein the polymer comprises at least one monomer of general formula I A-(CRR')$_n$-B wherein A is a polymerizable group; B is a ferrocenyl group; each of R and R' is independently selected from the group consisting of H and lower alkyl; and n is an integer less than about 20.

6. A method according to claim 1, wherein the electric potential is a cathodic potential.

7. A method according to claim 6, wherein the cathodic potential is from about 0 to about −0.1 V vs. Ag/AgCl.

8. A method according to claim 1, wherein the sample has a pH of about 3.5 to about 7.5.

9. A method according to claim 1 wherein the peroxide analyte is contained in a sample comprising an organic solvent.

10. A method according to claim 1 wherein the sample is not deaerated.

11. A method according to claim 1 wherein the selective detection of the peroxide analyte occurs without interference from any oxygen, ascorbic acid or uric acid present in the sample.

12. A method according to claim 1, wherein the electrode substrate is selected from the group consisting of metal, carbon, and screen printed electrode substrates.

13. A method according to claim 1, wherein the electrode substrate is selected from the group consisting of platinum, gold, glassy carbon, and graphite.

* * * * *

UNITED STATES PATENT AND TRADEMARK OFFICE
CERTIFICATE OF CORRECTION

PATENT NO. : 5,938,917
DATED : August 17, 1999
INVENTOR(S) : Ashok Kitmatrai Mulchandani It is certified that error appears in the above-identified patent and that said Letters Patent is hereby corrected as shown below:

Column 1,
After the title insert:

-- STATEMENT REGARDING FEDERALLY SPONSORED RESEARCH OR DEVELOPMENT

This invention was made with government support under NSF Grant No. BCS-9309741 awarded by the National Science Foundation. The Government has certain rights in this invention. --

Signed and Sealed this

Twenty-second Day of April, 2003

JAMES E. ROGAN
*Director of the United States Patent and Trademark Office*